United States Patent [19]

Lauder et al.

[11] 4,009,242
[45] Feb. 22, 1977

[54] METAL OXYHALIDE CATALYZED REACTIONS

[75] Inventors: Alan Lauder, Newark; Elrey L. McCann, III, Wilmington, both of Del.

[73] Assignee: E. I. Du Pont de Nemours and Company, Wilmington, Del.

[22] Filed: Apr. 8, 1975

[21] Appl. No.: 566,106

[52] U.S. Cl. .............................. 423/213.2; 252/462; 260/680 R; 260/690; 423/239; 423/245; 423/247
[51] Int. Cl.$^2$ .......................................... B01J 23/10
[58] Field of Search ............ 423/213.2, 213.5, 239, 423/245, 247; 252/441, 462, 466 PT; 260/687, 690

[56] References Cited

UNITED STATES PATENTS

| | | | |
|---|---|---|---|
| 3,133,029 | 5/1964 | Hoekstra | 423/213.2 X |
| 3,367,888 | 2/1968 | Hoekstra | 423/213.5 X |
| 3,741,725 | 6/1973 | Graham | 423/213.5 |
| 3,897,367 | 7/1975 | Lauder | 423/213.5 X |
| 3,901,828 | 8/1975 | Mai et al. | 423/213.5 X |

*Primary Examiner*—G. O. Peters

[57] ABSTRACT

Oxidation and reduction reactions using metal oxyhalide catalysts of the general formula $ABO_{3-f}X_f$ having perovskite-type crystal structures in which A and B are each cations of at least one metal and a portion of the type B cations are catalytically active; X is fluoride or chloride; and f is about from 0.01 to 2.5.

3 Claims, No Drawings

METAL OXYHALIDE CATALYZED REACTIONS

BACKGROUND OF THE INVENTION

Many metal oxides and other metal-based compositions are known as heterogeneous catalysts for gas and liquid phase oxidation and reduction reactions in the chemical process and petroleum refining industries. However, these catalyst compositions often deteriorate in use, losing their crystallographic identity or active components through volatilization, poisoning or crystallite growth.

For example, catalytic reforming requires catalysts that provide active acidic sites such as halogen. These acid sites in conventional reforming and hydrocracking catalysts are continuously lost during operation, with concomitant loss in catalyst utility.

Moreover, current environmental concerns require catalysts capable of converting the objectionable components of industrial and automotive exhaust streams to innocuous substances. Known catalysts have generally been unable to withstand the reducing atmospheres, high temperatures, and anti-knock additive residues commonly found in such applications.

SUMMARY OF THE INVENTION

The present invention provides an improvement for oxidation-reduction reactions found in a wide variety of chemical processes, petroleum refining applications, and exhaust stream conversions through the use of a catalyst which exhibits high thermal stability and enhanced resistance to reducing environments and chemical poisoning.

Specifically, the present invention provides an improvement in the process of bringing into contact at least one oxidizable reactant and at least one reducible reactant in the presence of a catalyst and under such conditions as to effect a change in oxidation state of at least one reactant, which improvement comprises bringing the reactants into contact in the presence of at least one catalytic compound of the general formula $ABO_{3-f}X_f$ and having the perovskite crystal structure wherein A and B are each cations of at least one metal and at least about 1% of the Type B cations are derived from at least one catalytically active metal selected from metals of Groups VB, VIB, VIIB, VIII and IB of the Periodic Table; O is oxide; X is fluoride or chloride; and $f$ is about from 0.01 to 2.5.

Preferably, the A and B cation sites are occupied by ions which contribute to the catalytic activity or stability of the compounds.

DETAILED DESCRIPTION OF THE INVENTION

The metal oxyhalides used in the present invention have a perovskite crystalline configuration.

Ideal perovskite structures contain cations of appropriate relative sizes and coordination properties and have cubic crystalline forms in which the corners of the unit cubes are occupied by the larger Type A cations (each coordinated with twelve oxide ions), the centers of the cubes are occupied by the smaller Type B cations (each coordinated with six oxide ions), and the faces of the cubes are occupied by oxide ions. Variations and distortions of this fundamental cubic crystal structure are known among materials commonly considered to be perovskites or perovskite-like. Distortions of the cubic crystal structure of perovskite and perovskite-like metal oxides include rhombohedral, orthorhombic, pseudocubic, tetragonal, and pseudotetragonal modifications. In all these crystal structures, it is required that the total number of A site cations should substantially equal the total number of B site cations, also that the combined charge of the cations substantially equal the charge on the oxygen atoms.

The particular B site metals and A site metals present depend to some degree upon the radii of the metal cations. The importance of ionic radii in perovskite crystal structures has been discussed by many authors, e.g., by Krebs in "Fundamentals of Inorganic Crystal Chemistry," McGraw Hill, London (1968). The Type A cations of the present compositions generally exhibit ionic radii of from about 0.8 to 1.65 Angstroms, while the Type B cations generally have ionic radii of from about 0.4 to 1.4 Angstroms. The ionic radii referred to herein are those tabulated by Shannon and Prewitt, Acta Cryst. B25 925 (1969) and B26 1046 (1970).

In the oxyhalides used in the invention, the same compositional ion size, and steric relationships pertain except that a fraction of the divalent oxygen ions of the $ABO_3$ type perovskite crystal lattice has been replaced by monovalent halogen selected from fluoride and chloride in amounts corresponding to an "f" value in the formula of about from 0.01 to 2.5. Amounts of halide corresponding to an $f$ value of about from 0.01 to 1.0 can also be used to advantage.

The perovskite-type metal oxyhalides used herein thus have the general emperical formula $ABO_{3-f}X_f$, in which the total number of A cations substantially equals the total number of B cations and the combined charge of the A and B cations substantially equals the combined charges of the oxide and halide ions.

In general, the stoichiometric requisites for the metals, oxygen and halogen in the compounds of the present invention are met. However, the present compounds can contain defect structures with an excess or a deficiency of metal ions of up to about 25 atomic percent of the requisite for the ideal $ABO_{3-f}X_f$ perovskite crystal structure without seriously detracting from their desirable characteristics. Since the halide valence of one is less than the oxide valence of two, the electrical neutrality of the composition can be achieved, if needed, by one or both of the following techniques. Two or more cations having different valences can be selected for incorporation into the A or B sites, or one or more cations capable of assuming different valence states can be selected for use in the compounds.

The particular cations of Type A used in the present compositions are not critical provided they exhibit suitable ionic radii and are otherwise capable of entering into perovskite formation along with the other components making up the crystal lattice. Included are mono-, d-, tri- and tetravalent cations. Thus, the metals of Type A can be selected from metals of the Periodic Table Groups IA, IB, IIA, IIB, IIIB, and IVA, and VA, from the lanthanide rare earth metals (atomic numbers 58 through 71) and from the actinide rare earth metals (atomic numbers 90 through 104).

Preferably they are cations of metals whose first ionization potential is not greater than about 6.90, i.e., metals of Groups IA, IIA, IIIB, the rare earth series and the actinide series, in particular Na, K, Ca, Sr, Ba, La or a mixture of cations of lanthanide rear earth metals. One such mixture of lanthanide rare earth metals contains about one-half cerium, one-third lanthanum, one-sixth neodymium, and smaller amounts of the remaining metals of atomic numbers 58 through 71. These metals provide still greater stability to the present compounds.

The cations of Type B also can be selected from any cations having suitable ionic radii and are otherwise capable of entering into the perovskite crystalline structure. At least 1% of these cations should be those derived from metals selected from Groups VB, VIB, VIIB, VIII, IB and IIB of the Periodic Table. Particular catalystic benefit is obtained through the use of cations derived from catalytic metals having atomic numbers 23 to 30, that is, Cr, Mn, Fe, Co, Ni, Zn and Cu, and the platinum metals, Ru, Rh, Pd, Os, Pt and Ir. The polyvalent metals of atomic numbers 23 to 29 and the platinum metals platinum and ruthenium provide increased catalytic effect, and are therefore preferred.

Catalytic metals other than the platinum group metals are preferably present in amounts corresponding to at least about 10% of the B sites. When the catalytic metal ions include one or more platinum group metal ions, either as the sole catalytic material or as a component of a mixture of catalytic material, the platinum group metal will normally comprise from about 1 to 20% of the B type metals.

Ruthenium, osmium, rhodium and iridium are capable of occupying all of the Type B cation sites in perovskite crystal structures, but little additional benefit is achieved when more than about 20% of the sites are occupied by these metals. Palladium and platinum ions are larger than ruthenium, osmium, rhodium and iridium ions and generally not more than about 10% of the Type B sites of crystalline oxides of the $ABO_{3-f}X_f$ type can be occupied by the ions of these metals with retention of a perovskite structure. Palladium is typically divalent; rhodium is typically trivalent; ruthenium, iridium and platinum are typically tetravalent; and osmium can have a valence of four, five, six or seven in these compounds. Mixtures of the platinum metals obtained by the partial refining of their ores can also be used in these compounds.

Many of these catalytic metals can exhibit two or more valences differing in increments of 1 or 2 valence units. Compounds containing these metals are generally more active catalysts, possibly because these metals are capable of existing in perovskite crystal structures in two or three valences differing by one valence unit increments. Catalysts of the present invention wherein a Type B metal is present in two valences often exhibits increased catalytic activity over similar compounds in which the metal is present in only a single valence, possibly because of the enhanced electron mobility through their crystal structures resulting from the presence of a variable-valence metal. For this reason too it may often be advantageous to employ such variable-valent catalytic components along with platinum metal catalytic components in the compositions of this invention. In such embodiments, at least about 5% of the B sites will be occupied by a variable-valent metal in a first valence and at least about 5% by the same metal in a second valence, the valences differing preferably by one unit.

Any B type sites not occupied by the catalytic metals can be occupied by other cations of metals from Groups IA, IIA, IIIA, IIIB, IVA, IVB and VA of the Periodic Table having the proper ion size and valence for the particular composition contemplated. Examples are Li and Na of Group IA; Mg, Cr, and Sr of Groups IIA, B; Al, Ga, In, Sc and La of Groups IIIA, B; Ti, Zr, Hf and Sn if Groups IVA; and Sb of Group VA. The B metals sodium, magnesium, calcium, strontium, aluminum, tin and antimony are relatively abundant and can be present in major proportions with relatively small reductions in the catalytic activity contributed to these compounds by other less readily available metals and, therefore, represent relatively inexpensive diluents in such compounds. For maximum contribution to crystal lattice stability, it is preferred to employ filler cations of metals whose first ionization potential is not greater than 7.10 (i.e., metals of Groups IA, IIA, IIIA, IIIB, the rare earth series, the actinide series and IVB, preferably not greater than 6.90. Aluminum imparts to perovskite crystal structures a high degree of thermal stability, resistance to lattice reduction in a reducing atmosphere and durability in catalytic applications, and is accordingly particularly preferred as a diluent material.

The Periodic Table to which reference is made herein is that given at pages 448-449, "Handbook of Chemistry and Physics", 40th Edition, Chemical Rubber Publishing Company (1958-9).

It is generally preferred that the several components of the compositions used in the present invention be selected as to their nature and proportions such that the Lattice Stability Index (LSI) value of the composition is minimized and is not greater than about 13.2 electron volts, and preferably, not greater than 12.0. In general, lower LSI values indicate more stable catalytic compositions.

The LSI values are the sum of the products of (a) the atomic fraction of each A site cation and each B site cation times (b) the first ionization potential of each such metal. Accordingly, the LSI value is calculated by the following equation:

$$LSI = f_a{}^1 \cdot I_a{}^1 + f_a{}^2 \cdot I_a{}^2 \cdots + f_a{}^i \cdot I_a{}^i + f_b{}^1 \cdot I_b{}^1 + f_b{}^2 \cdot I_b{}^2 \cdots + I_b{}^i \cdot f_b{}^i$$

wherein $f_a{}^1, f_a{}^2, f_a{}^i, f_b{}^1, f_b{}^2, f_b{}^i$ are the atomic fractions of cations $A^1, A^2, -A^i, B^1, B^2, -B^i$, respectively, $I_a{}^1, I_a{}^2 - I_a{}^i$ are the first ionization potentials of the metals corresponding to the A site cations and $I_b{}^1, I_b{}^2 - I_b{}^i$ are the first ionization potentials of the metals corresponding to the B site cations involved. When a variable-valence metal is present in a composition, an atomic fraction is assigned to the amount of the metal in each valence consistent with the requirements of electrical neutrality of the present compositions.

By ionization potential is meant the gas phase first ionization potential of the element as given by Vedeneyev et al, "Bond Energies, Ionization Potentials and Electron Affinities," St. Martin's Press (1966).

The compositions used in this invention can be prepared by heating mixtures of metal oxides and/or precursors thereof with metal halides that are thermally stable below 900° C. and relatively involatile under substantially anhydrous conditions for sufficient times and temperatures which permit spontaneous formation of the compositions. The metal compounds will provide the desired metal oxygen and halide moieties and preferably will be used in the stoichiometric proportions corresponding to the composition desired. The oxide-providing starting materials include not only the oxides themselves but such precursors as the carbonates, carboxylates (acetates, oxalates, tartrates), nitrites and nitrates which are converted to oxides by prolonged heating in oxidizing atmospheres at the temperatures at which these compositions are formed.

A metal chloride or fluoride of one or more of the metals involved, which may be of the A type and/or the B type, in an amount providing the desired proportion of halogen in the final composition, can be admixed with the rest of the perovskite-forming components, preferably in the form of the metallic carbonates coprecipitated from aqueous solution, the metal moieties of said material being of the A and/or B types as needed and in the desired proportions to complete the perovskite formulation.

The present compounds are in many instances formed by atomic diffusion, without melting of any of the starting or potential intermediate materials, and are subject to coating of unreacted particles by reaction products. Accordingly, the mixture of materials which are heated should generally be finely subdivided and intimately mixed before heating, and thoroughly ground and mixed by any conventional techniques several times during the heating period. The heating times and temperatures required for the formation of significant amounts of these catalytic compounds depend upon the particular compositions being formed, the times required usually being shorter at higher temperatures. Temperatures above about 900° C. are usually suitable for the formation of these compounds, using firing times of hours to days with occasional intermediate grinding and mixing, but temperatures of from 500° to 1500° C. can also be used.

The coated perovskite compositions used in the invention can be used in the form of free-flowing powders, for example, in fluid-bed reaction systems, or in the form of shaped structures providing efficient contact between the catalyst and reactant gases. The catalyst compositions can contain minor or major amounts of catalytically inert materials, with the catalytic compositions primarily on the surfaces of the inert material or dispersed throughout. For example, the powdered compounds can be formed into porous catalyst pellets in which they are dispersed throughout by conventional techniques employing pellet presses, rolling mixers or extruders. Dispersants, lubricants, and binders are often used in conjunction with the preparation of such pellets.

One particularly useful dispersant-binder for use in forming extruded pellet catalyst structures containing the catalyst compositions described herein is a high-purity alpha alumina monohydrate sold by the Continental Oil Co. as "Dispal". This material is a white, free-flowing powder of small particle size formed of very fine ultimate crystallites having a surface area of about 200 square meters per gram and a bulk density of 45 to 50 pounds per cubic foot. It forms thixotropic dispersions at concentrations of about 3% to 30% in water containing about 4 to 6% commercial concentrated (37% HCl) hydrochloric acid based on the weight of alumina, which dispersions become thicker upon standing. Thick dispersions containing about 20 to 30 parts of the alumina monohydrate and about 100 to 150 parts of acidified water per 100 parts of a catalytic composition having a surface area of about two square meters per gram can be extruded through small orifices to obtain structures which retain their form when wet and have significant strength when dried of gross water and heated at about 500° C. to about 900° C. to remove at least a part of the water present in the alumina monohydrate.

Catalytic compositions of this invention are preferably used in the form of coatings on suitable refractory supports. Such supports can be composed solely or primarily of silica, of ceramic compositions having softening or melting temperatures above the temperatures involved in forming or coating these catalytic compositions on such supports, of natural silicious materials such as diatomaceous earths and pumice, as well as of alundum, gamma alumina, silicon carbide, titania, zirconia, and other such refractory materials.

The compositions used in the present invention can be applied to supports either before or after the completion of the catalytic compositions. For example, the perovskite substrates of the present catalytic compositions can be formed on supports which are sufficiently high melting and non-reactive to withstand the subsequent processing steps involved in the application of the catalytic metal oxide compositions to the perovskite substrate. Alternatively, the catalytic composition of the invention can be preformed and applied to the support structure in a slurry. A particularly useful dispersant-binder for use in such slurry-coating processes is the "Dispal" alpha alumina monohydrate described above as a dispersant-binder useful in making extruded catalyst structures. Typically, acidified dispersions containing about 4 to 10% alpha alumina hydrate and a comparable amount of the ground catalytic compositions are prepared, pieces of the support material are coated with the dispersion, the coated pieces are dried, and the dried coated pieces are heated to a temperature and for a time (e.g., for 2 to 24 hours at 500° C. to 900° C.) to remove at least a portion of the water from the alpha alumina monohydrate.

The metal oxyhalide catalysts are used in accordance with the present invention to promote oxidation and reduction reaction in which the oxidation state of at least one reactant is changed. Especially beneficial processes involve the oxidation of oxidizable carbon components to compounds of higher oxidation states, the reduction of carbon monoxide and of nitrogen oxides to compounds of lower oxidation states and the reduction of hydrocarbyl mercaptans and sulfides to substantially sulfur-free hydrocarbon compositions.

Incorporation of the halide component into the perovskite structure as defined provides active (acidic) metal-halide groups in the crystal lattice, which groups constitute the kind of reaction sites considered important in reforming and hydrocracking petroleum chemical operations, but can be employed as a valuable means of providing catalytically active metals in more than one valence state (differing by a charge of one) in the same crystal lattice, which splitting of the valence states can be beneficial in promoting those reactions which depend on the presence in the catalyst of a metal in two or more valence states for higher catalytic activity.

Among the oxidation processes of the present invention is the oxidation of carbon monoxide to carbon dioxide and of hydrocarbons to carbon dioxide. Hydrocarbons which can be used include those having 1-20 carbon atoms, including those that are normally gaseous and those that can be entrained in a gaseous stream such as the liquefied petroleum gases and the volatile aromatic, olefinic and paraffinic hydrocarbons which are commonly in industrial solvents and in fuels for internal combustion engines. The oxidant for these processes can be oxygen, nitrogen oxides, such as NO and $NO_2$, which components are normally present in the exhaust gases of internal combustion engines.

A further process of this invention is the use of the required catalysts in the reduction of such oxides of nitrogen as nitric oxide, nitrogen dioxide, dinitrogen trioxide, dinitrogen tetroxide and the higher oxides of nitrogen such as may be present in waste gases from the production and use of nitric acid as well as in the exhaust gases of internal combustion engines. The reductant for these processes can be hydrogen, carbon monoxide and such hydrocarbons as described above and as present in said exhaust gases.

The metal oxyhalides of this invention containing ruthenium are particularly useful as catalysts for the reduction of nitrogen oxides. They generally catalyze the reduction of these oxides to innocuous compounds (e.g., nitrogen) instead of to ammonia. Metal oxyhalides containing platinum and palladium are particularly useful as catalysts for the complete oxidation of carbon compounds to carbon dioxide.

Thus the processes of this invention further include the oxidation of carbon monoxide and volatile hydrocarbons and for the simultaneous reduction of oxides of nitrogen under conditions typical of those involved in the cleanup of the exhaust gases of automotive and other internal combustion engines and are capable of effecting the substantially complete conversion of the obnoxious components of such gases to innocuous substances.

Still another hydrocarbon oxidation process of this invention is the steam reforming of hydrocarbons. This process known also as hydrocarbon reforming involves reaction of methane or a homolog thereof such as those found in volatile naphthas with steam in the presence of a catalyst of the invention. Those containing Ni or Co or a platinum metal selected from Pd, Pt, Ir, Ru and Rh supported on alumina, magnesia, or a basic oxide composition are particularly well suited for this application. The resulting product stream contains CO and $H_2$, normally accompanied by $CO_2$ formed by reaction of CO with excess steam in the well-known water gas shift. Reaction temperatures are normally in the range 450 to 1,000° C., usually not above 900° C., at pressures up to about 700 psi and usually at least about 100 to 200 psi for methane reforming at reactant ratios of from about 1.5 to 6 moles of steam per carbon in the hydrocarbon feed stock.

Another process of this invention is the water gas shift reaction which involves reaction of CO with $H_2O$ (steam) at moderately elevated temperatures. Particularly suitable are those catalysts contains cations of the first transition metal series, such as Fe, Co, Ni or Cu, preferably Fe or Cu. The resulting product-stream is depleted in CO and containing $CO_2$ and H. Temperatures in general are in the 200° to 500° C. range, with higher conversions favored at the lower temperatures, higher reaction rates at the higher temperatures. The process appears to be largely independent of pressure.

Still another hydrocarbon oxidation process that can be catalyzed by metal oxyhalides as described herein is the dehydrogenation of aliphatic, cycloaliphatic and alkylaromatic hydrocarbons having 4 to 12 carbon atoms and at least two saturated (i.e., nonolefinic and nonaromatic) —CH— groups which are adjacent or in 1,6-positions relative to one another (corresponding to said first oxidation state) to hydrocarbons, usually of the same carbon content, formed by removal of the hydrogens from one or more pairs of said -CH- groups (corresponding to said second oxidation state). Included are the dehydrogenation of such aliphatic hydrocarbons as butane and 2-methylbutane to such olefins and diolefins as butene, 2-methylbutene, butadiene and 2-methylbutadiene; cyclodehydrogenation of alkanes having removable hydrogens as defined and preferably having six -CH- groups in a chain, such as n-hexane, 2,3- and 4-methylhexane, n-heptane and various methylheptanes to the corresponding cyclohexanes, including methyl-substituted cyclohexanes; dehydroaromatization of cyclohexane and the methyl-substituted cyclohexanes to benzenoid hydrocarbons such as benzene, toluene and the xylenes; dehydroaromatization of decalins to naphthalenes; dehydrogenation of alkyl side chains of alkylbenzenes such as ethylbenzene to form styrene.

Reaction conditions generally involve temperatures in the range of 400° to 700° C. and solid catalysts as described herein, particularly those containing Group VIII platinum metals, especially Pt. The reaction can be conducted in the presence of oxygen or in the absence of oxygen and in the presence of hydrogen gas as in the well-known catalytic reforming process of the petroleum refining industry. The presence of halogen in the catalysts of this invention substantially reduces or eliminates the need for the addition of halogen-containing compounds to the feed stream to be dehydrogenated.

In the important catalytic reforming process of the petroleum refining industry, a relatively low octane value feed stream containing dehydrocyclizable and aromatizable hydrocarbons is converted into a relatively high octane value exit stream containing aromatic hydrocarbons of the gasoline boiling range as the essential components resulting primarily from dehydrocyclization of open-chain components to cyclohexanes and aromatization of cyclohexanes. Accompanying reactions include hydrocracking to lower carbon content components and isomerization of straight-chain to higher octane value branched-chain components. The process is generally carried in the presence of hydrogen to suppress side reactions leading to carbonization and to produce a composition which is largely saturated except for the aromatic hydrocarbon content.

The feed stream normally comprises alkanes and cycloalkanes having 4–12 carbons, preferably 5–10 carbons, and including (a) one or more open-chain compounds having 6–8 carbons and at least six —CH— groups in a chain, such as n-hexane, n-heptane and the methyl-substituted derivatives thereof described above, and/or preferably (b) one or more cyclopentanes having 1–3 methyl substituents on different ring carbons, such as methylcyclopentane, 1,2-dimethyl-, 1,3-dimethyl- and 1,2,4-trimethylcyclopentane, which are isomerizable into cyclohexane and methyl-substituted cyclohexanes, hence aromatizable into the corresponding benzenoid hydrocarbons. A typical feed stream composed as above will have a research octane number in the range 40–85, more usually 50–70. In these reactants, the oxidizable and the reducible reactant are represented by the same compound.

The reforming reaction is normally conducted at about 450° to 550° C. and at pressures of about 200 to 900 psi and if desired in the presence of added hydrogen gas in amounts corresponding to 3–15 moles per mole of feed to minimize side reactions.

The product stream comprises the so-called reformate fraction, rich in high octane value aromatics, such as benzene, toluene and the xylenes and having a typical research octane number in the 88–103 range, accompanied by an essentially saturated gaseous fraction rich in $C_1$–$C_4$ alkanes and hydrogen gas, a valuable by-product for use in various hydrotreating processes, e.g., hydrodesulfurization.

Still further processes that can be catalyzed in accordance with this invention are those Fischer-Tropsch reactions involving the reduction of carbon monoxide with hydrogen in the presence of a metal oxyhalide catalyst as defined, particularly those containing Fe, Co, Ni, or Ru at elevated temperatures (usually 150° to 600° C.) and pressures (up to 15,000 psi) effective to produce one or more products containing chemically bound C and H with or without chemically bound such as methane or one or more gaseous, liquid or solid higher hydrocarbons, with or without alcohols, aldehydes, ketones and fatty acids. One embodiment comprises the well-known methanation reaction generally conducted at about 200° to 600° C. at elevated pressures, typically about 50 to 500 psi, preferably over a Ni-containing metal oxyhalide catalyst of this invention. Suitable feed streams include the product stream from the steam reforming of methane, containing CO, $H_2$, reacted steam and some $CO_2$ formed in the water gas shift. Another embodiment widely used for the production of liquid fuels in the gasoline and diesel fuel ranges involves reaction of CO with $H_2$ at relatively low temperatures, such as 150° to 400° C. and pressures in the range of about 15 to 300 psi, preferably over metal oxyhalides containing Fe or Co ions, which promote the formation of hydrocarbons higher than $CH_4$, especially the liquid fractions suitable as fuels for internal combustion engines. The reaction products may sometimes include partially reduced, i.e., oxygenation products such as alcohols, aldehydes, ketones and carboxy acids, as produced in accordance with the Fischer-Tropsch process variation known as the synthol process.

Another reduction process catalyzed by oxyhalides defined herein is the catalytic desulfurization or hydrogenalysis of organic divalent sulfur compounds, such as those naturally occurring in feed stocks used in the petroleum chemical industry, for example, those used for the production of synthesis gas (CO and $H_2$) by steam reforming as described earlier, which stocks include mercaptans, linear sulfides, cyclic sulfides and the aromatic cyclic sulfide thiophene.

The feed stock desulfurization reaction is normally conducted at temperatures of 150–500° C., preferably 300°–400° C., over a wide range of pressures, including atmospheric, in the presence of a cobalt oxyhalide catalyst and in the presence of 2 large excess of $H_2$ relative to the sulfur content of the feed stock, typical proportions being 0.25 to 1.0 mole of $H_2$ per average mole of feed stock hydrocarbon corresponding generally to 250–1,000 mole of $H_2$ per S atom in the feed.

The reaction product comprises hydrogen sulfide gas and a substantially sulfur-free hydrocarbon composition. The $H_2S$ can be removed by means described in the art, as by physical stripping or by chemical absorption, e.g., by ZnO to product ZnS.

The invention is further illustrated by the following specific examples, in which parts and percentages are by weight unless otherwise indicated.

EXAMPLES 1–21

The catalytic compositions used in the processes of Examples 1–21 were prepared by heating mixtures of precursor compounds containing appropriate stoichiometric amounts of the metals and halogens involved. The mixed precursor compounds were obtained by one of two procedures, as indicated in Table I:

Procedure A: An aqueous potassium carbonate solution was added to an aqueous solution of metal nitrates and the resulting insoluble materials were separated, washed, dried, and ground and a powdered low-volatility halogen compound (e.g., aluminum fluoride, lanthanum chloride, or thorium fluoride) was added.

Procedure B: An aqueous potassium carbonate solution was added to a slurry of a powdered water-insoluble low-volatility compound (e.g., aluminum fluoride, molybdenum oxide, or platinum oxide) in an aqueous solution of metal nitrates and the resulting insoluble materials were separated, washed, dried, and ground. The mixed precursor compounds were heated in crucibles in air at 900° or 1,000° C. for several days with occasional cooling, grinding, and mixing. The resulting metal oxide compositions were finely ground. The expected perovskite structures of the products were confirmed by their x-ray diffraction patterns.

TABLE I

Metal Oxyhalides

| Example | Metal Oxyhalide | Preparation Procedure |
|---|---|---|
| 1,2,3 | $[La][Fe_{0.8}Al_{0.2}]O_{2.8}F_{0.2}$ | A |
| 4,5,6 | $[La][Cr_{0.8}Al_{0.2}]O_{2.9}Cl_{0.1}$ | B |
| 7,8,9 | $[La_{0.2}Ba_{0.8}][Cu_{0.5}Al_{0.1}Mo_{0.4}]O_{2.7}F_{0.3}$ | B |
| 10,11,12 | $[La_{0.9}Th_{0.1}][Fe_{0.5}Cr_{0.5}]O_{2.6}F_{0.4}$ | A |
| 13,14,15 | $[La_{0.5}Sr_{0.5}][Al_{0.9}Pt_{0.1}]O_{2.6}F_{0.4}$ | B |
| 16,17,18 | $[La_{0.5}Sr_{0.5}][Al_{0.9}Pt_{0.1}]O_{2.6}Cl_{0.4}$ | B |
| 19,20,21 | $[La_{0.75}Sr_{0.25}][Al_{0.4}Pt_{0.1}Co_{0.5}]O_{2.6}F_{0.4}$ | A |

The catalysts were applied to supports for use in oxidation and reduction reactions. One part of "Dispal" M alumina dispersant and binder (obtained from the Continental Oil Company; surface area about 164 square meters per gram, determined with nitrogen by the Brunauer-Emmett-Teller method) was mixed with 17 parts of water containing a few drops of commercial concentrated hydrochloric acid. To this mixture was added 7.5 parts of the catalytic composition to obtain a stable thixotropic slurry. A cylinder of "Torvex" alumina ceramic honeycomb with straight-through cells (obtained from E. I. du Pont de Nemours & Company) was soaked in water. This cylinder weighed about 6 to 7 grams, was about 2.5 centimeters in diameter and thickness and nominally had a cell size of one-sixteenth inch, wall thickness of 0.018 inch, open area of 50%, 253 hexagonal holes per square inch, and a nominal geometric surface area of 462 square feet per cubic foot. The water-soaked cylinder was dipped into the slurry of the catalytic composition, the gross excess of slurry was removed by blowing the cylinder with air, the cylinder was dried, and the cylinder coated with the catalytic composition and binder was heated for about 30 minutes in air in a muffle furnace at about 700° C. The cylinder was again soaked in water, dipped into the slurry, blown free of excess slurry, and dried and then heated in air at about 700° C. for two hours. The percentage increase in weight of the cylinder due to the adherent catalytic composition and binder was about 15–25%.

The compositions were used in the reduction of nitric oxide by carbon monoxide. The "Torvex" ceramic honeycomb cylinder coated with the catalytic composition and binder was installed in a stainless steel chamber with a nominal internal diameter of 2.5 centimeters, height of 2.5 centimeters, and volume of 12.3 cubic centimeters. Nitrogen containing about 2,000 parts per million of nitric oxide and about 10,000 parts per million of carbon monoxide was passed through the chamber at a nominal hourly space velocity of about 40,000 hr.$^{-1}$ and pressure of one pound per square inch gauge while the feed gas and the catalyst chamber were heated so that the temperature of the gas entering the catalyst chamber increased from about 60° C. to about 600° C. over about 90 minutes. Samples of the inlet and exit gases were obtained periodically. The nitric oxide in these samples was oxidized to nitrogen dioxide. The resulting gas mixture was analyzed and the percent reduction in the nitric oxide concentration of the gas upon passing through the catalyst chamber was calculated. A smooth plot was made of the degree of conversion of nitric oxide at different catalyst chamber inlet temperatures for each catalytic composition. From a smooth curve through each plot, temperatures were estimated for "light-off" (the intercept with the temperature axis of an extrapolation of the portion of the curve at which the degree of conversion changed rapidly with temperature) and for nitric oxide conversions of 25%, 50%, and 90%. The catalyst temperature was higher than the catalyst bed inlet temperature with all the catalytic compositions at nitric oxide conversions greater than about 25%. Table II gives the estimated temperatures for light-off and for 25, 50, and 90% conversion of nitric oxide before and after heating the catalyst-coated honeycomb cylinders for 100 hours at about 900° C.

The catalytic compositions were used in the oxidation of carbon monoxide in a similar apparatus and by a similar procedure. Nitrogen containing about 10,000 parts per million of carbon monoxide and 10,000 parts per million of oxygen was passed through the catalyst chamber and the entering and exiting gas mixtures were analyzed chromatographically using a column containing granules of "Linde" 13X molecular sieve. The estimated temperatures for light-off and for 25, 50, and 90% conversion of carbon monoxide before and after heating the catalyst-coated honeycomb cylinders for 100 hours at about 900° C. are given in Table II.

The "Torvex" cylinders coated with the catalytic composition was used in the oxidation of propane in a similar apparatus and by a similar procedure. Nitrogen containing about 1,300 parts per million of propane was determined in a similar apparatus and by a similar procedure. Nitrogen containing about 1,300 parts per million of propane and 8,800 parts per million of oxygen was passed through the catalyst chamber and the entering and exiting gases were analyzed chromatographically using a column containing 80–100 mesh "Poropak" Q. The temperatures for light-off and for 25, 50, and 90% conversion of propane before and after heating the catalyst-coated honeycomb cylinders for 100 hours at about 900° C. are given in Table II.

TABLE II

| | Catalytic Activity | | | | | | | |
|---|---|---|---|---|---|---|---|---|
| Hours at 900° C | | 0  100 | 0  100 | 0 | 0 | 0  100 | 0  100 | 0  100 |
| | Example | 1 | 4 | 7 | 10 | 13 | 16 | 19 |
| Reduction of Nitric Oxide | "Light-off" temp., ° C | 290  345 | 305  350 | 270 | 325 | 285  240 | 290  380 | 395  385 |
| | 25% conversion, ° C | 365  545 | 375  405 | 305 | 400 | 320  405 | 320  410 | 435  420 |
| | 50% conversion, ° C | 445  — | 445  455 | 340 | 470 | 350  435 | 350  440 | 470  460 |
| | 90% conversion, ° C | 570  — | 595  — | 400 | 575 | 405  490 | 395  490 | 570  515 |
| | Example | 2 | 5 | 8 | 11 | 14 | 17 | 20 |
| Oxidation of Carbon Monoxide | "Light-off" temp., ° C | 270  285 | 235  335 | 270 | 285 | 205  190 | 225  240 | 295  225 |
| | 25% conversion, ° C | 310  360 | 340  425 | 305 | 310 | 230  255 | 240  250 | 310  245 |
| | 50% conversion, ° C | 350  400 | 405  495 | 340 | 335 | 250  280 | 255  265 | 330  270 |
| | 90% conversion, ° C | 415  500 | 555  — | 475 | 380 | 290  320 | 275  285 | 355  305 |
| | Example | 3 | 6 | 9 | 12 | 15 | 18 | 21 |
| Oxidation of Propane | "Light-off" temp., ° C | 390  350 | 415  430 | 525 | 390 | 325  390 | 350  550 | 375  325 |
| | 25% conversion, ° C | 490  595 | 565  — | 585 | 495 | 505  505 | 500  0 | 455  490 |
| | 50% conversion, ° C | 560  — | —  — | — | 550 | 545  575 | 555  — | 535  575 |
| | 90% conversion, ° C | —  — | —  — | — | — | —  — | —  — | —  — |

Small samples (about 60 to 80 milligrams) of each of the metal oxyhalides used in Examples 1–6, and 13–21 were heated in a Du Pont Model 950 Thermogravimetric Analyzer in an atmosphere containing 1% hydrogen, 4% carbon monoxide, and 95% nitrogen (by volume, flowing at a rate of 30 milliliters per minute), with the temperature increasing in a programmed manner at a rate of 10° C. per minute to a final temperature of 1,000° C. The changes in weight given in Table III indicate the stability of the crystal structures of the Example metal oxyhalides under the experimental conditions. With the oxyfluorides:
 a. The metal oxyfluoride [La][Fe$_{0.8}$Al$_{0.2}$]O$_{2.6}$F$_{0.4}$ (Examples 1–3) did not change significantly in weight.
 b. The metal oxyfluorides used in Examples 13–15 and 19–21 decreased in weight by 5.9% and 2.6% and did not significantly increase in weight in any temperature region up to 1,000° C. The metal oxychlorides showed larger changes in weight than the metal oxyfluorides.

The x-ray diffraction patterns of all these metal oxyhalides contained the same strong lines after heating in the reducing atmosphre to 1,000° C. as before heating.

TABLE III

Stability of Metal Oxyhalides in a Reducing Atmosphere

| Example | Metal Oxylialide | Change in Weight (Based on Weight at 50–200° C) | | | | Total % | Direction of Change at 1000° C |
|---|---|---|---|---|---|---|---|
| | | Increase | | Decrease | | | |
| | | Temp. Range, °C | % | Temp. Range, °C | % | | |
| 1–3 | $[La][Fe_{0.8}Al_{0.2}]O_{2.8}F_{0.2}$ | None | None | 800–1000 | 0.2 | 0.2 | None |
| 4–6 | $[La][Cr_{0.8}Al_{0.2}]O_{2.9}Cl_{0.1}$ | 370–670 | 3.3 | 300–370 | 1.9 | 6.1 | Rapid Decrease |
| | | | | 670–780 | 2.3 | | |
| | | | | 780–1000 | 4.2 | | |
| 13–15 | $[La_{0.5}Sr_{0.5}][Al_{0.9}Pt_{0.1}]O_{2.6}F_{0.4}$ | None | None | 160–190 | 0.6 | 2.6 | None |
| | | | | 190–1000 | 2.0 | | |
| 16–18 | $[La_{0.5}Sr_{0.5}][Al_{0.9}Pt_{0.1}]O_{2.6}Cl_{0.4}$ | None | None | 35–160 | 1.4 | 10.5 | Slight Decrease |
| | | | | 160–300 | 3.9 | | |
| | | | | 500–1000 | 5.4 | | |
| 19–21 | $[La_{0.75}Sr_{0.25}][Al_{0.4}Pt_{0.1}Co_{0.5}]O_{2.6}F_{0.4}$ | None | None | 200–550 | 2.3 | 5.9 | Slight Decrease |
| | | | | 600–1000 | 3.6 | | |

We claim:

1. In the process of bringing into contact a gaseous stream comprising at least one oxidizable and at least one reducible reactant selected from oxygen, hydrogen, carbon monoxide, hydrocarbons and nitrogen oxides in the presence of a catalyst and under such conditions as to effect a change in the oxidation state of at least one reactant, the improvement which comprises bringing the reactants into contact in the presence of at least one catalytic compound of the general formula $ABO_{3-f}X_f$ and having a perovskite crystal structure, wherein A and B are each cations of at least one metal and at least about 1% of the Type B cations are derived from at least one catalytically active metal selected from metals of Groups VB, VIB, VIIB, VIII, IB and IIB of the Periodic Table; O is oxide; X is fluoride or chloride; and $f$ is about from 0.01 to 2.5.

2. A process of claim 1 wherein a stoichiometric excess of reducible reactants is present in the gaseous stream and the cations of catalytically active metal comprise platinum cations.

3. A process of claim 1 wherein a stoichiometric excess of oxidizable reactants is present in the gaseous stream and the cations of catalytically active metal comprise ruthenium cations.

* * * * *